United States Patent
Misumi et al.

(10) Patent No.: US 6,750,176 B2
(45) Date of Patent: Jun. 15, 2004

(54) WETTABLE COMPOSITIONS FOR USE IN AGRICULTURE, PREPARATION METHOD THEREFOR, AND STORAGE METHOD THEREFOR

(75) Inventors: Yuji Misumi, Ogasa-gun (JP); Katsushi Toyooka, Iwata (JP); Satoshi Watanabe, Fujinomiya (JP); Tsutomu Shimizu, Ogasa-gun (JP); Kozo Nagayama, Kakegawa (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/265,270

(22) Filed: Oct. 7, 2002

(65) Prior Publication Data

US 2004/0067851 A1 Apr. 8, 2004

(51) Int. Cl.$^7$ ............ A01N 63/04; C12N 1/04; C12N 1/14
(52) U.S. Cl. ............ 504/117; 424/93.5; 435/254.1; 435/256.1; 435/256.7
(58) Field of Search ............ 504/117; 424/93.5; 435/254.1, 256.1, 256.7; 514/93.5

(56) References Cited

FOREIGN PATENT DOCUMENTS

| JP | 63-227507 | | 9/1988 |
| JP | 4-368306 | | 12/1992 |
| JP | 5-236941 | * | 9/1993 |
| JP | 7-267811 | | 10/1995 |
| JP | 8-175919 | | 7/1996 |
| JP | 2000-264807 | | 9/2000 |
| JP | 2000-264808 | | 9/2000 |
| WO | 00/00017 | * | 1/2000 |

* cited by examiner

Primary Examiner—S. Mark Clardy
(74) Attorney, Agent, or Firm—Oblon, Spivak, McClelland, Maier & Neustadt, P.C.

(57) ABSTRACT

The present invention provides a wettable composition for use in agriculture comprising microorganisms as an active ingredient, which can maintain a high survival rate of the same over long periods, and exhibit superior physical properties during applications, and provide a method for stably storing the wettable composition for use in agriculture for a long period of time. That is, the present invention corresponds to a wettable composition for use in agriculture comprising spores of filamentous fungi which are in the form of dried powders having a volume median diameter ranging from 2 $\mu$m to 10 $\mu$m, and having a ratio of (volume 90% diameter)/(volume 10% diameter;) of not more than 5.62, and an adsorbent having a water absorption ability in an amount of at least 1% by mass based on the total mass of the composition. The composition is prepared by pulverizing and mixing a mixture of spores of filamentous fungi, an adsorbent having a water absorption ability, and other additive components such as a surfactant, in an appropriate ratio of the same, by means of impact pulverization, and adjusting a moisture content so that the moisture content is less than 2.5% by mass based on the total mass of the composition. In addition, the composition is stored by packaging in a bag formed from a hermetic film.

18 Claims, No Drawings

WETTABLE COMPOSITIONS FOR USE IN AGRICULTURE, PREPARATION METHOD THEREFOR, AND STORAGE METHOD THEREFOR

BACKGROUND OF THE INVENTION

1. Field of the Invention

The present invention relates to a wettable composition for use in agriculture, which comprises filamentous fungi as an active ingredient, which can stably store spores of the filamentous fungi over long periods and which exhibits good physical properties during application, relates to a method for effectively preparing the same, and relates to a method for stably storing the wettable compositions for use in agriculture over long periods.

2. Description of Related Art

Controlling plant diseases and plant pests are indispensable activities for effective agricultural production. In order to do this, synthetic agricultural chemicals have been employed, thereby resulting in good control. However, recently, due to applications of large amounts and various kinds of synthetic agricultural chemicals, resistant pests have arisen and environmental disruption has occurred, and these have become the subjects of discussion. For these reasons, an important problem to be solved in the field of agriculture is to provide methods for effectively and continuously carrying out agricultural production while decreasing the environmental burden.

As one means for solving the problem, microbial pesticides utilizing activities of microorganisms have been proposed. By employing the same alone or in combination with synthetic agricultural chemicals, effects of decreasing the environmental burden and effects of inhibiting frequency of occurrence of resistant diseases and pests, which are serious problems with synthetic agricultural chemicals, can be observed.

At present, as microorganisms anticipated to be used in microbial pesticides, avirulent Fusarium which controls diseases by activating inherent resistance in plants (Japanese Unexamined Patent Application, First Publication No. Hei 7-267811), Trichoderma exhibiting antibiosis to pathogenicity (The Ministry of Agriculture, Forestry, and Fisheries of Japan, Registration No. 7023), bacteria infecting weeds (Japanese Unexamined Patent Application, First Publication No. Hei 4-368306), and the like have been proposed.

As described above, various microorganisms having potentials for use in pesticides have been proposed. For developing microbial preparations, a key point is the ability to stably formulate the microorganisms as an active ingredient in a viable state in view of serious problems such as the death of microorganisms during storage. For this reason, an important problem to be solved is to develop methods for stably storing microorganisms over long periods in a viable state.

In addition, in the formulations of pesticides employing powders of dried microorganisms, it is necessary to prepare uniform suspensions, or powders or granules exhibiting good wettability and coating properties, for effective applications and treatments of the pesticides.

Wettable powders in the formulations of synthetic agricultural chemicals comprise an active ingredient; a solid carrier, examples of which include oxides such as diatomaceous earth or slaked lime, phosphates such as apatite, sulfates such as gypsum, fine powders of mineral materials such as talc, pyroferrite, clay, kaolin, bentonite, acid clay, white carbon, quartz powder, quartzite powder, or the like; and a small amount of surfactant. In the formulations of pesticides comprising powders of dried microorganisms as an active ingredient, it is preferable that they be employed in the form of a wettable powder as described above.

As methods for storing microorganisms, in general, a freeze-drying method, a liquid paraffin fold layer method, an inclined medium method, and the like are known. They are effective in the case of employing microorganisms on a small scale. However, they are not suitable for use as a method for storing microbial pesticides in which large amounts of microorganisms are treated and a high survival rate of the fungi is required.

On the other hand, as microbial pesticides or formulations comprising microbial materials, heretofore, a formulation wherein microorganisms of avirulent Fusarium are adsorbed to a zeolite-based base material, followed by air drying (Japanese Unexamined Patent Application, First Publication No. Sho 63-227507), a composition for controlling plant diseases utilizing spore fractions of bacteria belonging to the genus Bacillus (Japanese Unexamined Patent Application, First Publication No. Hei 8-175919), a composition in which microorganisms having effects of controlling plant diseases are mixed with an adsorbent having an ammonia absorbing power (Japanese Unexamined Patent Application, First Publication No. 2000-264808 and Japanese Unexamined Patent Application, First Publication No. 2000-264807), and the like are known.

Unfortunately, in the above-mentioned formulations comprising living microorganisms belonging to the genus Fusarium adsorbed to a zeolite-based base material, the rate of survival of the fungi tends to rapidly decrease when the formulation is stored at room temperature. In the case of the compositions for controlling plant diseases utilizing spore fractions of bacteria belonging to the genus Bacillus, the storage stability of the same has not been known at all. In addition, in the case of the microbial materials, the materials used as culture media are employed as they are, and for this reason, there is a problem in that nutritive components are present, thus promoting the growth of pathogens during storage. On the other hand, in the above-mentioned compositions comprising an adsorbent having an ammonia adsorbing ability, an unadsorbed carrier, that is, a free carrier having an adsorbing ability such as zeolite or silica gel in a state having an adsorbing ability exhibits strong hydrophobic properties, and for this reason, during application of the pesticides, and in particular, during dressing treatment of seeds, or in the case of application using water, inconvenience occurs.

BRIEF SUMMARY OF THE INVENTION

Under these circumstances, an object of the present invention is to provide a wettable composition for use in agriculture comprising microorganisms which can be viable at a high survival rate over long periods and exhibit good physical properties during application, as an active ingredient, and provide a method for stably storing the wettable composition for use in agriculture over long periods.

After diligent research with respect to microbial pesticides, and in particular, wettable compositions for use in agriculture, the present inventors discovered that a wettable composition comprising spores of filamentous fungi having a specific particle size distribution, and an adsorbent having a specific amount of a water absorption ability, as essential ingredients, exhibits good storage properties of the living fungi and exhibits good physical properties during application, discovered that the compositions can be effectively produced by subjecting the mixture comprising the required amounts of the components described above to an impact pulverization treatment, and discovered that by sealing the above-mentioned wettable composition in an impermeable bag, the composition can be stably stored over long periods, thus completing the present invention.

That is, the present invention provides a wettable composition for use in agriculture comprising spores of filamentous fungi which are in the form of dried powders having a volume median diameter ranging from 2 μm to 10 μm, and having a ratio of (volume 90% diameter)/(volume 10% diameter) of not more than 5.62, and an adsorbent having a water absorption ability, wherein the adsorbent having a water absorption ability is added in an amount of at least 1% by mass based on the total mass of the composition, provides a method for preparing a wettable composition for use in agriculture, comprising the steps of preparing a mixture of the above-described spores of filamentous fungi, an adsorbent having a water absorption ability, and other additive components, in an appropriate ratio of the same, pulverizing and mixing the mixture by means of impact pulverization, and adjusting a water content so that the water content is less than 2.5% by mass based on the total mass of the composition, and provides a method for storing a wettable composition for use in agriculture, comprising the steps of sealing the wettable composition for use in agriculture described above in a bag formed of a hermetic film.

DETAILED DESCRIPTION OF THE INVENTION

The wettable compositions for use in agriculture according to the present invention comprise spores of filamentous fungi which are in the form of dried powders having a volume median diameter ranging from 2 $\mu$m to 10 $\mu$m, and having a ratio of (volume 90% diameter)/(volume 10% diameter) of not more than 5.62, and an adsorbent having a water absorption ability, as essential ingredients. The filamentous fungi described above are not particularly restricted, and for example, filamentous fungi selected from those belonging to the genus Trichoderma and the genus Aspergillus are employed.

In the wettable compositions of the present invention, spores of the filamentous fungi described above are employed. The filamentous fungi are preferably living fungi comprising conidia or chlamydospores as a principal component. In the living fungi, mycelia may be present. In the present invention, the entire culture including the spores described above may be employed as it is, or it may be employed after being finely powdered. In addition, spores isolated from the culture may be employed.

The media for use in the culture of the filamentous fungi are not particularly restricted, and can be arbitrarily selected from those commonly employed for culturing microorganisms. If the media are able to grow spores, either liquid media or solid media can be employed. As examples of the media, mention may be made of, for example, potato dextrose media, oatmeal media, common agar media, yeast extract/malt extract agar media, and solid component media derived from plants. As the solid components derived from plants, grains, beans, or residues of the same are preferably employed. For example, solid components such as wheat, rice, beans and bran, rice bran, soybean residue, bean-curd refuse, azuki bean residue, peanut residue, and the like can be employed as medium components.

Employing the media which have the optimal conditions as media, after sterilization, the filamentous fungi are inoculated, followed by shaking culture or stationary culture for approximately 1 to 30 days at an optimal growing temperature. Thereby, a culture with a high concentration of spores can be obtained.

In the compositions of the present invention, with respect to the number of the spores of filamentous fungi included therein, conidia or chlamydospores are included at a rate commonly ranging from 10 to $10^{10}$, preferably ranging from $10^3$ to $10^9$, and more preferably ranging from $10^5$ to $10^8$ based on 1 g of the composition. It should be understood that the number of spores is not restricted to these ranges.

It is preferable that the filamentous fungi employed in the present invention be in the form of dried powders. The powders having, in common, a particle size of approximately 1 to 45 $\mu$m and particularly having a volume median diameter of 2 to 10 $\mu$m, and having a particle size distribution in which the ratio of (volume 90% diameter)/(volume 10% diameter) is less than or equal to 5.62 are suitable. Here, the term "volume median diameter" means a median diameter of the cumulative value of the volume diameters. That is, the term "a ratio of (volume 90% diameter)/(volume 10% diameter)" means a numerical value calculated by dividing volume 90% diameter of a cumulative volume diameter commonly employed (accumulation from the small particle size to the large particle size) by volume 10% diameter.

Next, the adsorbents having a water absorption ability, employed in the present invention, may be those having a water adsorption ability and be in the form of a solid, and are not particularly restricted. The substances having a water adsorption ability for adsorbing moisture in an amount of 10% or more by mass with respect to the mass of the adsorbent having a water absorption ability are preferable. As examples of the adsorbents described above, mention may be made of, for example, synthetic zeolites, inorganic materials such as attapulgite, galeonite, bentonite, and the like, inorganic metal salts, which can form hydrous salts, such as sodium sulfate, calcium chloride, sodium carbonate, and the like, and in addition, activated carbon, silica gel, activated alumina, and the like. In particular, synthetic zeolite, silica gel, and activated alumina are suitable.

In common, these adsorbents preferably have a particle size ranging from 0.01 $\mu$m to 100 $\mu$m. In particular, the adsorbents having a particle size distribution in which those having a particle size of 75 $\mu$m or less are present in an amount of 90% or more by mass are preferable.

In the compositions of the present invention, the added amount of the above-mentioned adsorbent having a water absorption ability is preferably 1% or more by mass based on the total mass of the composition. If the amount is below 1% by mass, sufficient stabilizing effects on spores of filamentous fungi cannot be exhibited. Considering stabilizing effects of spores of filamentous fungi, physical properties during application, and the like, it is preferable that as an adsorbent having a water absorption ability, a synthetic zeolite be employed in an amount of 1 to 25% by mass, a silica gel be employed in an amount of 50 to 95% by mass, or an activated alumina be employed in an amount of 10 to 95% by mass, based on the total mass of the composition. At least two kinds selected from the synthetic zeolite, silica gel, and alumina described above can be simultaneously employed. In this case, the total amount of the adsorbents is employed in a range of 1 to 95% by mass, is preferably employed in a range of 5 to 95% by mass, and is more preferably employed in a range of 10 to 95% by mass, based on the total mass of the composition. In addition, in the case of employing adsorbents required to be activated in order to adsorb water, they are preliminarily subjected to an activation treatment in order to exhibit sufficient water absorption ability, and may then be employed.

As the surfactants employed in the present invention, those which are innocuous with respect to the employed spores of filamentous fungi or do not affect the fungi within a range of the added amount which can impart wettability and dispersibility to the compositions may be employed, and these are not particularly restricted. Among these surfactants, in the case of employing, as spores of filamentous fungi, dried powders having a volume median diameter of 2 μm to 10 μm, and having a particle size distribution in which a ratio of (volume 90% diameter)/(volume 10% diameter) is less than or equal to 5.62, the produced compositions may be hydrophobic, and for this reason, surfactants exhibiting superior wetting power are preferable in order to impart wettability to these compositions.

As examples of surfactants described above, mention may be made of, for example, nonionic surfactants such as polyethylene glycol higher fatty acid esters, polyoxyethylene alkyl ethers, polyoxyethylene alkyl aryl ethers, polyoxyethylene allyl phenyl ethers, sorbitan monoalkylates, or the like; anionic surfactants such as alkyl aryl sulfonates, dialkyl sulfonates, lignin sulfonates, naphthalene sulfonates and condensates of the same, alkyl sulfuric esters, alkyl phosphoric esters, alkyl aryl sulfuric esters, alkyl aryl phosphoric esters, polyoxyethylene alkyl ether sulfuric esters, polyoxyethylene alkyl aryl ether sulfuric esters, polyoxyethylene allyl phenyl ether phosphates, polycarboxylic acid type polymer activators, and the like; silicone-based surfactants; fluorine-based surfactants; soap surfactants; and the like.

Among these surfactants, lignin sulfonate based surfactants and polycarbonate based surfactants are, in particular, suitable.

These surfactants may be employed alone or in combination of two or more of the same. The added amount of the same is selected from a range commonly extending from 0.1 to 20% by mass, preferably from 0.5 to 10% by mass, and more preferably from 2 to 7% by mass, based on the total mass of the composition.

The silicone-based surfactants, fluorine-based surfactants, and soap surfactants may be employed as an antifoamer.

In the compositions of the present invention, a carrier can be further comprised as necessary, in addition to the spores of filamentous fungi, adsorbents having a water absorption ability, and optional surfactants, as described above. In this case, it is preferable that the carrier be innocuous with respect to the filamentous fungi or have no effect thereon.

As the carriers described above, a water-soluble carrier or a water-insoluble carrier can be employed. As examples of water-soluble carriers, mention may be made of, for example, salts of organic or inorganic acids such as ammonium sulfate, ammonium hydrogen carbonate, ammonium nitrate, ammonium chloride, potassium chloride, sodium sulfate, magnesium sulfate, sodium citrate, sodium carbonate, sodium hydrogen carbonate, and the like; organic acids such as citric acid, succinic acid, and the like; saccharides such as sucrose, lactose, and the like; urea; and the like.

On the other hand, as examples of water-insoluble carriers, mention may be made of, for example, mineral powders such as clays, calcium carbonate, talc, diatomaceous earth, bentonite, and the like; non-mineral powders such as white carbon, and the like; starches; wheat flour; and the like. In addition, the adsorbents having a water absorption ability described above can be employed as a carrier. Among these carriers, in particular, clays are preferable. In addition, the added amount of the carrier is preferably selected from a range of 10 to 85% by mass based on the total mass of the composition.

In addition, in the case where the compositions of the present invention are formed as a wettable composition in the form of granules, it is advantageous to add a binder. The binders are not particularly restricted, and may be those conventionally employed in the formulations of granular compositions of pesticides. Preferably, water-soluble binders may be employed. As examples of the binders described above, mention may be made of carboxymethylcellulose sodium salt, dextrin, water-soluble starch, xanthan gum, guar seed gum, sucrose, polyvinylpyrrolidone, polyvinyl alcohol, and the like.

The added amount of the binders is commonly selected from a range of 0.01 to 10% by mass, and is preferably selected from a range of 0.1 to 5% by mass, based on the total mass of the composition.

In the compositions of the present invention, it is desirable that the moisture content be less than 2.5% by mass, and preferably be 1.75% or less by mass, based on the total mass of the composition. If the moisture content is 2.5% or more by mass, the storage stability of the spores of filamentous fungi may be insufficient.

Preparation of the wettable compositions for use in agriculture of the present invention can be carried out according to a common method for preparing a wettable powder of pesticides. For example, the wettable compositions can be prepared by pulverizing and mixing a mixture comprising filamentous fungi, an adsorbent having a water absorption ability, and other additive components, in an appropriate ratio of the same. In this case, if all of the components already have a grain size which does not require pulverization, simply mixing the components can yield a wettable composition for use in agriculture which is sufficient for practical use. Taking into consideration the physical properties during application of the compositions described above, it is advantageous that pulverizing and mixing be carried out by means of a grinder. In this case, pulverizing methods which adversely affect the survival of the spores of filamentous fungi are not preferable. Therefore, it is preferable that pulverizing and mixing be carried out by means of impact type pulverization using a common impact type grinder such as a hammer or a pulverizing ring.

In addition, preparation of the wettable compositions can be carried out as follows. Each of the components other than the spores of filamentous fungi is preliminarily subjected to impact pulverization or pulverization in high-speed air to form granulated powders. Subsequently, powders of dried spores of filamentous fungi are added thereto, followed by uniform mixing thereof.

The wettable compositions for use in agriculture of the present invention, produced as described above, are preferably in the form of powders comprising 90% or more by mass of granulated powders having a particle size of 45 μm or less, and are more preferably in the form of fine powders having a volume median diameter of 1 μm to 25 μm, and in particular, preferably having a volume median diameter of 2 μm to 15 μm.

In addition, the formulations of the wettable compositions in the form of granules are prepared by mixing filamentous fungi, an adsorbent having a water absorption ability, and other additive components such as a surfactant, a binder, and the like in an appropriate ratio of the same, pulverizing the mixture as necessary, followed by granulation according to the common granulation methods such as an extrusion granulation method, a fluidized bed granulation method, a spray drying granulation method, a rolling granulation method, a dry compaction, and the like. The methods other than those described above may also be employed. The formulations of the wettable compositions for use in agriculture according to the present invention are preferably granules comprising 90% or more by mass of granules having a particle size of 45 µm to 1000 µm, and are, in particular, preferably granules comprising 90% or more by mass of granules having a particle size of 100 µm to 850 µm.

The wettable compositions for use in agriculture according to the present invention may be produced under common atmospheres employing common auxiliary materials, and may be packaged. The raw materials stored over long periods at high temperatures and high humidity and having high moisture content due to moisture absorption, and preparation and packaging at high temperatures and high humidity are not preferable. It is advantageous to select the raw materials and produce a composition so that the moisture content is preferably less than 2.5% by mass and is more preferably 1.75% or less by mass, based on the total mass of the composition.

When the wettable compositions for use in agriculture according to the present invention are stored, they may be stored by filling them in a packaging bag made of a material, which is gas impermeable, such as an aluminized bag, with a nitrogen gas. In addition, the wettable compositions for use in agriculture according to the present invention can be packaged by a water-soluble film made of a polyvinyl alcohol, in order to prevent the powders from scattering during dilution. In this case, the package including the composition packaged by the water-soluble film may be further packaged in a packaging bag made of a material, which is gas impermeable, such as an aluminized bag, with a nitrogen gas.

The wettable compositions for use in agriculture according to the present invention are commonly employed by diluting them in water at the time of use, or alternatively, are employed as they are in the form of wettable powders.

The wettable compositions for use in agriculture according to the present invention can be employed according to the methods commonly used in pesticide applications, at the time of use. That is, the wettable compositions for use in agriculture according to the present invention are employed by diluting them in water, for example, approximately by 50 to 20,000 times. Alternatively, the compositions can also be employed in seed dressing treatments with a small amount of water or without water.

The wettable compositions for use in agriculture according to the present invention are in the form of a solid. For this reason, they can be produced at room temperature, and can be stored over long periods and be distributed. Even after storage and distribution, the initial effects can be maintained. In addition, they have a usability equivalent to that of common synthetic agricultural chemicals, and can be widely employed with ease in common farms. In addition, the spores of the filamentous fungi in the wettable compositions for use in agriculture according to the present invention simply coexist with the adsorbents having a water absorption ability, and are not adsorbed or carried on the adsorbents. For this reason, they can rapidly exhibit the effects.

EXAMPLES

In the following, the present invention is described in detail with the Examples and Test Examples. It should be understood that the present invention is not restricted to these Examples.

In the Examples and Comparative Examples, *Trichoderma atroviride* SKT-1 (deposited as FERM P-16510 in the Microorganism Industry Research Center, Agency of Industrial Science and Technology, Ministry of International Trade and Industry), and *Aspergillus oryzae* IFO-5375, corresponding to a type strain stored in the Institute for Fermentation were employed as test fungi.

The volume median diameter and the particle size distribution of the powders of the dried fungi were measured by means of a laser device for measuring particle size distribution, LMS-24 (manufactured by Seishin Corporation) by suspending an appropriate amount of the powders in an aqueous solution including 0.5% by mass of calcium dodecylbenzene sulfonate. The amount of moisture included in the composition was measured by means of a Hiranuma measuring device for measuring a trace amount of moisture, AQ-7 (manufactured by Hiranuma Industries, Co., Ltd.) according to a Karl Fischer coulometric titration.

Example 1

Dried powders of conidia produced by liquid stationary culture of *Trichoderma atroviride* fungi (volume median diameter: 3.7 µm, ratio of (volume 90% diameter)/(volume 10% diameter): 3.85) in an amount of 2 parts by mass, calcium lignin sulfonate (Pearlex CP, produced by Nippon Paper Industries, Co., Ltd.) in an amount of 4 parts by mass, zeolite powders (Synthetic Zeolite A-3, pore size: 0.3 nm, produced by Tosoh Corporation) in an amount of 15 parts by mass, and clay (Fine Powdered Clay, produced by Showa Chemical Industries, Co., Ltd.) in an amount of 79 parts by mass were mixed by means of a bench mill, thus producing a wettable composition of microbial pesticide. The moisture content based on the total mass of the composition was 1.5% by mass.

Example 2

Dried powders of conidia produced by liquid stationary culture of *Trichoderma atroviride* fungi (volume median diameter: 3.7 µm, ratio of (volume 90% diameter)/(volume 10% diameter): 3.85) in an amount of 2 parts by mass, a polycarbonate-based surfactant (New Cargen WG 5, produced by Takemoto Oil & Fat, Co., Ltd.) in an amount of 4 parts by mass, zeolite powders (Synthetic zeolite A-3, pore size: 0.3 nm, produced by Tosoh Corporation) in an amount of 25 parts by mass, and clay (Fine Powdered Clay, produced by Showa Chemical Industries, Co., Ltd.) in an amount of 69 parts by mass were mixed by means of a bench mill, thus producing a wettable composition of microbial pesticide. The moisture content based on the total mass of the composition was 1.3% by mass.

Example 3

Dried powders of conidia produced by liquid stationary culture of *Trichoderma atroviride* fungi (volume median diameter: 3.7 µm, ratio of (volume 90% diameter)/(volume 10% diameter): 3.85) in an amount of 2 parts by mass, a polycarbonate-based surfactant (New Cargen WG 5, produced by Takemoto Oil & Fat, Co., Ltd.) in an amount of 4 parts by mass, silica gel powders in an amount of 94 parts by mass were mixed by means of a bench mill, thus producing a wettable composition of microbial pesticide. The moisture content based on the total mass of the composition was 1.2% by mass.

Example 4

Dried powders of conidia produced by liquid stationary culture of *Trichoderma atroviride* fungi (volume median diameter: 3.7 µm, ratio of (volume 90% diameter)/(volume 10% diameter): 3.85) in an amount of 2 parts by mass, calcium lignin sulfonate (Pearlex CP, produced by Nippon Paper Industries, Co., Ltd.) in an amount of 4 parts by mass, silica gel powders in an amount of 50 parts by mass, and clay (Fine Powdered Clay, produced by Showa Chemical Industries, Co., Ltd.) in an amount of 44 parts by mass were mixed by means of a bench mill, thus producing a wettable composition of microbial pesticide. The moisture content based on the total mass of the composition was 1.5% by mass.

Example 5

Dried powders of conidia produced by liquid stationary culture of *Trichoderma atroviride* fungi (volume median diameter: 3.7 μm, ratio of (volume 90% diameter)/(volume 10% diameter): 3.85) in an amount of 2 parts by mass, calcium lignin sulfonate (Pearlex CP, produced by Nippon Paper Industries, Co., Ltd.) in an amount of 4 parts by mass, zeolite powders (Synthetic Zeolite A-3, pore size: 0.3 nm, produced by Tosoh Corporation) in an amount of 15 parts by mass, and clay (Fine Powdered Clay, produced by Showa Chemical Industries, Co., Ltd.) in an amount of 79 parts by mass were mixed by means of an impact grinder (hammer mill), thus producing a wettable composition of microbial pesticide. The moisture content based on the total mass of the composition was 1.5% by mass. The produced wettable composition of microbial pesticide in an amount of 100 g was charged in a water-soluble film bag made of polyvinyl alcohol, having a size of 20 cm length, 15 cm width, and 30 μm thickness, and the bag was sealed by means of a heat seal, thus producing a water-soluble film bag packaging a wettable composition of microbial pesticide.

Example 6

The wettable composition of microbial pesticide produced in Example 5 in an amount of 100 g was charged in a single-layered aluminized bag, having a size of 22 cm length and 16 cm width, and the bag was sealed by means of a heat seal, thus producing a bag packaging a wettable composition of microbial pesticide.

Example 7

The wettable composition of microbial pesticide produced in Example 3 in an amount of 100 g was charged in a single-layered aluminized bag, having a size of 22 cm length and 16 cm width, and the bag was sealed by means of a heat seal, thus producing a bag packaging a wettable composition of microbial pesticide.

Example 8

Dried powders of conidia produced by liquid stationary culture of *Aspergillus oryzae* fungi (volume median diameter: 6.6 μm, ratio of (volume 90% diameter)/(volume 10% diameter): 2.81) in an amount of 2 parts by mass, calcium lignin sulfonate (Pearlex CP, produced by Nippon Paper Industries, Co., Ltd.) in an amount of 4 parts by mass, zeolite powders (Synthetic Zeolite A-3, pore size: 0.3 nm, produced by Tosoh Corporation) in an amount of 15 parts by mass, and clay (Fine Powdered Clay, produced by Showa Chemical Industries, Co., Ltd.) in an amount of 79 parts by mass were mixed by means of a bench mill, thus producing a wettable composition of microbial pesticide. The moisture content based on the total mass of the composition was 1.6% by mass.

Example 9

Dried powders of conidia produced by liquid stationary culture of *Aspergillus oryzae* fungi (volume median diameter: 6.6 μm, ratio of (volume 90% diameter)/(volume 10% diameter): 2.81) in an amount of 2 parts by mass, a polycarbonate-based surfactant (New Cargen WG 5, produced by Takemoto Oil & Fat, Co., Ltd.) in an amount of 4 parts by mass, zeolite powders (Synthetic zeolite A-3, pore size: 0.3 nm, produced by Tosoh Corporation) in an amount of 25 parts by mass, and clay (Fine Powdered Clay, produced by Showa Chemical Industries, Co., Ltd.) in an amount of 69 parts by mass were mixed by means of a bench mill, thus producing a wettable composition of microbial pesticide. The moisture content based on the total mass of the composition was 1.4% by mass.

Example 10

Dried powders of conidia produced by liquid stationary culture of *Aspergillus oryzae* fungi (volume median diameter: 6.6 μm, ratio of (volume 90% diameter)/(volume 10% diameter): 2.81) in an amount of 2 parts by mass, a polycarbonate-based surfactant (New Cargen WG 5, produced by Takemoto Oil & Fat, Co., Ltd.) in an amount of 4 parts by mass, and silica gel powders in an amount of 94 parts by mass were mixed by means of a bench mill, thus producing a wettable composition of microbial pesticide. The moisture content based on the total mass of the composition was 1.4% by mass.

Example 11

Dried powders of conidia produced by liquid stationary culture of *Aspergillus oryzae* fungi (volume median diameter: 6.6 μm, ratio of (volume 90% diameter)/(volume 10% diameter): 2.81) in an amount of 2 parts by mass, calcium lignin sulfonate (Pearlex CP, produced by Nippon Paper Industries, Co., Ltd.) in an amount of 4 parts by mass, silica gel powders in an amount of 50 parts by mass, and clay (Fine Powdered Clay, produced by Showa Chemical Industries, Co., Ltd.) in an amount of 44 parts by mass were mixed by means of a bench mill, thus producing a wettable composition of microbial pesticide. The moisture content based on the total mass of the composition was 1.3% by mass.

Example 12

Dried powders of conidia produced by liquid stationary culture of *Aspergillus oryzae* fungi (volume median diameter: 6.6 μm, ratio of (volume 90% diameter)/(volume 10% diameter): 2.81) in an amount of 2 parts by mass, calcium lignin sulfonate (Pearlex CP, produced by Nippon Paper Industries, Co., Ltd.) in an amount of 4 parts by mass, zeolite powders (Synthetic Zeolite A-3, pore size: 0.3 nm, produced by Tosoh Corporation) in an amount of 15 parts by mass, and clay (Fine Powdered Clay, produced by Showa Chemical Industries, Co., Ltd.) in an amount of 79 parts by mass were mixed by means of an impact grinder (hammer mill), thus producing a wettable composition of microbial pesticide. The moisture content based on the total mass of the composition was 1.6% by mass. The produced wettable composition of microbial pesticide in an amount of 100 g was charged in a water-soluble film bag made of polyvinyl alcohol, having a size of 20 cm length, 15 cm width, and 30 µm thickness, and the bag was sealed by means of a heat seal, thus producing a water-soluble film bag packaging a wettable composition of microbial pesticide.

Example 13

The wettable composition of microbial pesticide produced in Example 12 in an amount of 100 g was charged in a single-layered aluminized bag, having a size of 22 cm length and 16 cm width, and the bag was sealed by means of a heat seal, thus producing a bag packaging a wettable composition of microbial pesticide.

Example 14

The wettable composition of microbial pesticide produced in Example 10 in an amount of 100 g was charged in a single-layered aluminized bag, having a size of 22 cm length and 16 cm width, and the bag was sealed by means of a heat seal, thus producing a bag packaging a wettable composition of microbial pesticide.

Example 15

Dried powders of conidia produced by liquid stationary culture of *Trichoderma atroviride* fungi (volume median diameter: 3.7 µm, ratio of (volume 90% diameter)/(volume 10% diameter): 3.85) in an amount of 2 parts by mass, calcium lignin sulfonate (Pearlex CP, produced by Nippon Paper Industries, Co., Ltd.) in an amount of 4 parts by mass, activated alumina powders in an amount of 15 parts by mass, and clay (Fine Powdered Clay, produced by Showa Chemical Industries, Co., Ltd.) in an amount of 79 parts by mass were mixed by means of a bench mill. Subsequently, the mixture was formed into granules by means of dry compaction, thus producing a wettable composition of microbial pesticide. The moisture content based on the total mass of the composition was 1.5% by mass.

Example 16

Dried powders of conidia produced by liquid stationary culture of *Aspergillus oryzae* fungi (volume median diameter: 6.6 µm, ratio of (volume 90% diameter)/(volume 10% diameter): 2.81) in an amount of 2 parts by mass, a polycarbonate-based surfactant (New Cargen WG 5, produced by Takemoto Oil & Fat, Co., Ltd.) in an amount of 4 parts by mass, activated alumina powders in an amount of 50 parts by mass, and clay (Fine Powdered Clay, produced by Showa Chemical Industries, Co., Ltd.) in an amount of 44 parts by mass were mixed by means of a bench mill. Subsequently, the mixture was formed into granules by means of dry compaction, thus producing a wettable composition of microbial pesticide. The moisture content based on the total mass of the composition was 1.6% by mass.

Example 17

Dried powders of conidia produced by liquid stationary culture of *Trichoderma atroviride* fungi (volume median diameter: 3.7 µm, ratio of (volume 90% diameter)/(volume 10% diameter): 3.85) in an amount of 2 parts by mass, a polycarbonate-based surfactant (New Cargen WG 5, produced by Takemoto Oil & Fat, Co., Ltd.) in an amount of 4 parts by mass, zeolite powders (Synthetic Zeolite A-3, pore size: 0.3 nm, produced by Tosoh Corporation) in an amount of 5 parts by mass, clay (Fine Powdered Clay, produced by Showa Chemical Industries, Co., Ltd.) in an amount of 81 parts by mass, and wheat flours in an amount of 8 parts by mass were mixed by means of a bench mill, thus producing a wettable composition of microbial pesticide. The moisture content based on the total mass of the composition was 1.5% by mass.

Example 18

Dried powders of conidia produced by liquid stationary culture of *Trichoderma atroviride* fungi (volume median diameter: 3.7 µm, ratio of (volume 90% diameter)/(volume 10% diameter): 3.85) in an amount of 16 parts by mass, a polycarbonate-based surfactant (New Cargen WG 5, produced by Takemoto Oil & Fat, Co., Ltd.) in an amount of 4 parts by mass, zeolite powders (Synthetic Zeolite A-3, pore size: 0.3 nm, produced by Tosoh Corporation) in an amount of 5 parts by mass, clay (Fine Powdered Clay, produced by Showa Chemical Industries, Co., Ltd.) in an amount of 11 parts by mass, and wheat flours in an amount of 64 parts by mass were mixed by means of a bench mill, thus producing a wettable composition of microbial pesticide. The moisture content based on the total mass of the composition was 1.4% by mass.

Example 19

Dried powders of conidia produced by liquid stationary culture of *Trichoderma atroviride* fungi (volume median diameter: 3.7 µm, ratio of (volume 90% diameter)/(volume 10% diameter): 3.85) in an amount of 2 parts by mass, bentonite (Kunimibond, produced by Kunimine Industries, Co., Ltd.) in an amount of 2 parts by mass, and cane sugar (produced by Kanto Kagaku Co., Ltd.) in an amount of 96 parts by mass were mixed by means of a bench mill, thus producing a wettable composition of microbial pesticide. The moisture content based on the total mass of the composition was 1.6% by mass.

Example 20

Dried powders of conidia produced by liquid stationary culture of *Trichoderma atroviride* fungi (volume median diameter: 3.7 µm, ratio of (volume 90% diameter)/(volume 10% diameter): 3.85) in an amount of 2 parts by mass, a polycarbonate-based surfactant (New Cargen WG 5, produced by Takemoto Oil & Fat, Co., Ltd.) in an amount of 4 parts by mass, zeolite powders (Synthetic Zeolite A-3, pore size: 0.3 nm, produced by Tosoh Corporation) in an amount of 5 parts by mass, clay (Fine Powdered Clay, produced by Showa Chemical Industries, Co., Ltd.) in an amount of 69 parts by mass, and anhydrous sodium sulfate in an amount of 20 parts by mass were mixed by means of a bench mill, thus producing a wettable composition of microbial pesticide. The moisture content based on the total mass of the composition was 1.4% by mass.

Comparative Example 1

Dried powders of conidia produced by solid stationary culture of *Trichoderma atroviride* fungi (volume median diameter: 6.8 µm, ratio of (volume 90% diameter)/(volume 10% diameter): 5.99) in an amount of 2 parts by mass, zeolite powders (Synthetic Zeolite A-3, pore size: 0.3 nm, produced by Tosoh Corporation) in an amount of 25 parts by mass, and clay (Fine Powdered Clay, produced by Showa Chemical Industries, Co., Ltd.) in an amount of 73 parts by mass were mixed by means of a bench mill, thus producing a wettable composition of microbial pesticide.

Comparative Example 2

Dried powders of conidia produced by solid stationary culture of *Trichoderma atroviride* fungi (volume median diameter: 6.8 μm, ratio of (volume 90% diameter)/(volume 10% diameter): 5.99) in an amount of 2 parts by mass, and silica gel powders in an amount of 98 parts by mass were mixed by means of a bench mill, thus producing a wettable composition of microbial pesticide.

Comparative Example 3

Dried powders of conidia produced by solid stationary culture of *Trichoderma atroviride* fungi (volume median diameter: 6.8 μm, ratio of (volume 90% diameter)/(volume 10% diameter): 5.99) in an amount of 2 parts by mass, zeolite powders (Synthetic Zeolite A-3, pore size: 0.3 nm, produced by Tosoh Corporation) in an amount of 2 parts by mass, clay (Fine Powdered Clay, produced by Showa Chemical Industries, Co., Ltd.) in an amount of 94 parts by mass, and water in an amount of 2 parts by mass were mixed by means of a bench mill, thus producing a wettable composition of microbial pesticide. The moisture content based on the total mass of the composition was 2.7% by mass. The produced wettable composition of microbial pesticide in an amount of 100 g was charged in a single-layered aluminized bag, having a size of 22 cm length and 16 cm width, and the bag was sealed by means of a heat seal, thus producing a bag packaging a wettable composition of microbial pesticide.

Comparative Example 4

Dried powders of conidia produced by solid stationary culture of *Trichoderma atroviride* fungi (volume median diameter: 6.8 μm, ratio of (volume 90% diameter)/(volume 10% diameter): 5.99) in an amount of 2 parts by mass, a polycarbonate-based surfactant (New Cargen WG 5, produced by Takemoto Oil & Fat, Co., Ltd.) in an amount of 4 parts by mass, and clay (Fine Powdered Clay, produced by Showa Chemical Industries, Co., Ltd.) in an amount of 94 parts by mass were mixed by means of a bench mill, thus producing a wettable composition of microbial pesticide. The produced wettable composition of microbial pesticide in an amount of 100 g was charged in a single-layered aluminized bag, having a size of 22 cm length and 16 cm width, and the bag was sealed by means of a heat seal, thus producing a bag packaging a wettable composition of microbial pesticide.

Comparative Example 5

Dried powders of conidia produced by solid stationary culture of *Trichoderma atroviride* fungi (volume median diameter: 6.8 μm, ratio of (volume 90% diameter)/(volume 10% diameter): 5.99) in an amount of 2 parts by mass, silica gel powders in an amount of 2 parts by mass, and clay (Fine Powdered Clay, produced by Showa Chemical Industries, Co., Ltd.) in an amount of 96 parts by mass were mixed by means of a bench mill, thus producing a wettable composition of microbial pesticide. The produced wettable composition of microbial pesticide in an amount of 100 g was charged in a single-layered aluminized bag, having a size of 22 cm length and 16 cm width, and the bag was sealed by means of a heat seal, thus producing a bag packaging a wettable composition of microbial pesticide.

Comparative Example 6

Dried powders of conidia produced by solid stationary culture of *Trichoderma atroviride* fungi (volume median diameter: 6.8 μm, ratio of (volume 90% diameter)/(volume 10% diameter): 5.99) in an amount of 2 parts by mass, silica gel powders in an amount of 2 parts by mass, and clay (Fine Powdered Clay, produced by Showa Chemical Industries, Co., Ltd.) in an amount of 96 parts by mass were pulverized and mixed by means of a Jet-O-Mizer in a high-speed flow, thus producing a wettable composition of microbial pesticide.

Comparative Example 7

Dried powders of conidia produced by solid stationary culture of *Aspergillus oryzae* fungi (volume median diameter: 9.7 μm, ratio of (volume 90% diameter)/(volume 10% diameter): 15.82) in an amount of 2 parts by mass, zeolite powders (Synthetic Zeolite A-3, pore size: 0.3 nm, produced by Tosoh Corporation) in an amount of 25 parts by mass, and clay (Fine Powdered Clay, produced by Showa Chemical Industries, Co., Ltd.) in an amount of 73 parts by mass were mixed by means of a bench mill, thus producing a wettable composition of microbial pesticide.

Comparative Example 8

Dried powders of conidia produced by solid stationary culture of *Aspergillus oryzae* fungi (volume median diameter: 9.7 μm, ratio of (volume 90% diameter)/(volume 10% diameter): 15.82) in an amount of 2 parts by mass, and silica gel powders in an amount of 98 parts by mass were mixed by means of a bench mill, thus producing a wettable composition of microbial pesticide.

Comparative Example 9

Dried powders of conidia produced by solid stationary culture of *Aspergillus oryzae* fungi (volume median diameter: 9.7 μm, ratio of (volume 90% diameter)/(volume 10% diameter): 15.82) in an amount of 2 parts by mass, zeolite powders (Synthetic Zeolite A-3, pore size: 0.3 nm, produced by Tosoh Corporation) in an amount of 2 parts by mass, clay (Fine Powdered Clay, produced by Showa Chemical Industries, Co., Ltd.) in an amount of 94 parts by mass, and water in an amount of 2 parts by mass were mixed by means of a bench mill, thus producing a wettable composition of microbial pesticide. The moisture content based on the total mass of the composition was 2.9% by mass. The produced wettable composition of microbial pesticide in an amount of 100 g was charged in a single-layered aluminized bag, having a size of 22 cm length and 16 cm width, and the bag was sealed by means of a heat seal, thus producing a bag packaging a wettable composition of microbial pesticide.

Comparative Example 10

Dried powders of conidia produced by solid stationary culture of *Aspergillus oryzae* fungi (volume median diameter: 9.7 μm, ratio of (volume 90% diameter)/(volume 10% diameter): 15.82) in an amount of 2 parts by mass, a polycarbonate-based surfactant (New Cargen WG 5, produced by Takemoto Oil & Fat, Co., Ltd.) in an amount of 4 parts by mass, and clay (Fine Powdered Clay, produced by Showa Chemical Industries, Co., Ltd.) in an amount of 94 parts by mass were mixed by means of a bench mill, thus producing a wettable composition of microbial pesticide. The produced wettable composition of microbial pesticide in an amount of 100 g was charged in a single-layered aluminized bag, having a size of 22 cm length and 16 cm width, and the bag was sealed by means of a heat seal, thus producing a bag packaging a wettable composition of microbial pesticide.

Comparative Example 11

Dried powders of conidia produced by solid stationary culture of *Aspergillus oryzae* fungi (volume median diameter: 9.7 μm, ratio of (volume 90% diameter)/(volume 10% diameter): 15.82) in an amount of 2 parts by mass, silica gel powders in an amount of 2 parts by mass, and clay (Fine Powdered Clay, produced by Showa Chemical Industries, Co., Ltd.) in an amount of 96 parts by mass were mixed by means of a bench mill, thus producing a wettable composition of microbial pesticide. The produced wettable composition of microbial pesticide in an amount of 100 g was charged in a single-layered aluminized bag, having a size of 22 cm length and 16 cm width, and the bag was sealed by means of a heat seal, thus producing a bag packaging a wettable composition of microbial pesticide.

Comparative Example 12

Dried powders of conidia produced by solid stationary culture of *Aspergillus oryzae* fungi (volume median diameter: 9.7 μm, ratio of (volume 90% diameter)/(volume 10% diameter): 15.82) in an amount of 2 parts by mass, silica gel powders in an amount of 2 parts by mass, and clay (Fine Powdered Clay, produced by Showa Chemical Industries, Co., Ltd.) in an amount of 96 parts by mass were pulverized and mixed by means of a Jet-O-Mizer in a high-speed flow, thus producing a wettable composition of microbial pesticide.

Comparative Example 13

Dried powders of conidia produced by solid stationary culture of *Trichoderma atroviride* fungi (volume median diameter: 3.7 μm, ratio of (volume 90% diameter)/(volume 10% diameter): 5.99) in an amount of 2 parts by mass, activated alumina powders in an amount of 15 parts by mass, and clay (Fine Powdered Clay, produced by Showa Chemical Industries, Co., Ltd.) in an amount of 83 parts by mass were mixed by means of a bench mill. Subsequently, the mixture was formed into granules by means of dry compaction, thus producing a wettable composition of microbial pesticide.

Comparative Example 14

Dried powders of conidia produced by solid stationary culture of *Aspergillus oryzae* fungi (volume median diameter: 6.6 μm, ratio of (volume 90% diameter)/(volume 10% diameter): 15.82) in an amount of 2 parts by mass, activated alumina powders in an amount of 50 parts by mass, and clay (Fine Powdered Clay, produced by Showa Chemical Industries, Co., Ltd.) in an amount of 48 parts by mass were mixed by means of a bench mill. Subsequently, the mixture was formed into granules by means of dry compaction, thus producing a wettable composition of microbial pesticide.

Test Example 1

A composition of microbial pesticide in an amount of 0.1 g was introduced in a beaker of 100 mL volume including 100 mL of tap water. The time spent from the introduction of the composition to submergence of the entirety of the composition was measured. After completion of the submergence, the tap water into which the composition of microbial pesticide had been introduced was stirred along with the rim of the beaker at a rate of one rotation per second 30 times. Fifteen minutes after stirring, the suspension condition of the composition of microbial pesticide was observed by visual inspection.

In the compositions produced in Example 1, Example 4, Comparative Example 1, and Comparative Example 2, each of the compositions in an amount of 5 g was placed in a screw tube bottle made of glass of 20 mL volume, was stored for 60 days at 40° C., and was subsequently allowed to stand for 2 hours at room temperature, followed by the measurement of submergence time and the observation of suspension condition, according to the method described above. In addition, with respect to the packaged bags produced in Example 6, Example 7, and Comparative Example 5, each of the bags was stored for 60 days at 40° C., and was subsequently allowed to stand for 2 hours at room temperature, followed by the measurement of submergence time and the observation of suspension condition, according to the method described above. The results are shown in Table 1.

TABLE 1

| Example | | Submergence time | Suspension condition |
|---|---|---|---|
| 1 | Initial stage | 44 seconds | Uniform suspension, although there is a small amount of precipitate and suspended matter. |
|   | After 60 days at 40° C. | 29 seconds | Uniform suspension, although there is a small amount of precipitate and suspended matter. |
| 2 | Initial stage | 30 seconds | Uniform suspension, although there is a small amount of precipitate and suspended matter. |
| 3 | Initial stage | 91 seconds | Uniform suspension, although there is a small amount of precipitate and suspended matter. |
| 4 | Initial stage | 75 seconds | Uniform suspension, although there is a small amount of precipitate and suspended matter. |
|   | After 60 days at 40° C. | 57 seconds | Uniform suspension, although there is a small amount of precipitate and suspended matter. |
| 6 | Initial stage | 34 seconds | Uniform suspension, although there is a small amount of precipitate and suspended matter. |
|   | After 60 days at 40° C. | 27 seconds | Uniform suspension, although there is a small amount of precipitate and suspended matter. |
| 7 | Initial stage | 83 seconds | Uniform suspension, although there is a small amount of precipitate and suspended matter. |
|   | After 60 days at 40° C. | 64 seconds | Uniform suspension, although there is a small amount of precipitate and suspended matter. |
| 8 | Initial stage | 35 seconds | Uniform suspension, although there is a small amount of precipitate and suspended matter. |
| 9 | Initial stage | 41 seconds | Uniform suspension, although there is a small amount of precipitate and suspended matter. |
| 10 | Initial stage | 80 seconds | Uniform suspension, although there is a small amount of precipitate and suspended matter. |

TABLE 1-continued

| | | Submergence time | Suspension condition |
|---|---|---|---|
| 11 | Initial stage | 83 seconds | Uniform suspension, although there is a small amount of precipitate and suspended matter. |
| 15 | Initial stage | 76 seconds | Uniform suspension, although there is a small amount of precipitate and suspended matter. |
| 16 | Initial stage | 63 seconds | Uniform suspension, although there is a small amount of precipitate and suspended matter. |
| 17 | Initial stage | 54 seconds | Uniform suspension, although there is a small amount of precipitate and suspended matter. |
| 18 | Initial stage | 37 seconds | Uniform suspension, although there is a small amount of precipitate and suspended matter. |
| 19 | Initial stage | 1 second | Uniform suspension, although there is a small amount of precipitate. |
| 20 | Initial stage | 3 seconds | Uniform suspension, although there is a small amount of precipitate. |
| Comparative Example | | | |
| 1 | Initial stage | 300 or more seconds | Non-uniform suspension. There is a large amount of suspended matter, and precipitate is also observed. |
| | After 60 days at 40° C. | 300 or more seconds | Non-uniform suspension. There is a large amount of suspended matter, and precipitate is also observed. |
| 2 | Initial stage | 300 or more seconds | Non-uniform suspension. There is a large amount of suspended matter, and precipitate is also observed. |
| | After 60 days at 40° C. | 300 or more seconds | Non-uniform suspension. There is a large amount of suspended matter, and precipitate is also observed. |
| 5 | Initial stage | 300 or more seconds | Non-uniform suspension. There is a large amount of suspended matter, and precipitate is also observed. |
| | After 60 days at 40° C. | 300 or more seconds | Non-uniform suspension. There is a large amount of suspended matter, and precipitate is also observed. |
| 7 | Initial stage | 300 or more seconds | Non-uniform suspension. There is a large amount of suspended matter, and precipitate is also observed. |
| 8 | Initial stage | 300 or more seconds | Non-uniform suspension. There is a large amount of suspended matter, and precipitate is also observed. |
| 13 | Initial stage | 300 or more seconds | Non-uniform suspension. There is a large amount of suspended matter, and precipitate is also observed. |
| 14 | Initial stage | 300 or more seconds | Non-uniform suspension. There is a large amount of suspended matter, and precipitate is also observed. |

Test Example 2

Rice seeds in an amount of 50 g were immersed in tap water, and were then collected on a sieve, followed by standing for 15 minutes. After the moisture was taken away, the rice seeds were placed in an Erlenmeyer flask of 500 mL volume. A microbial pesticide composition in an amount of 0.25 g was added thereto, and the mixture was shaken by hand for 3 minutes. Subsequently, the coating condition was observed by visual inspection.

With respect to the compositions produced in Example 1, Example 4, Comparative Example 1, and Comparative Example 2, each of the compositions in an amount of 5 g was placed in a screw tube bottle made of glass, of 200 mL volume, and was stored for 60 days at 40° C. After the stored composition was allowed to stand for 2 hours at room temperature, the observation of the coating condition was carried out according to the test method described above.

TABLE 2

| | | Coating condition |
|---|---|---|
| Example | | |
| 1 | Initial stage | Uniform coating condition. Little clumping of rice seeds and little production of clumps only made from powders are observed. |
| | After 60 days at 40° C. | Uniform coating condition. Little clumping of rice seeds and little production of clumps only made from powders are observed. |
| 4 | Initial stage | Uniform coating condition. Little clumping of rice seeds and little production of clumps only made from powders are observed. |
| | After 60 days at 40° C. | Uniform coating condition. Little clumping of rice seeds and little production of clumps only made from powders are observed. |
| 8 | Initial stage | Uniform coating condition. Little clumping of rice seeds and little production of clumps only made from powders are observed. |
| 11 | Initial stage | Uniform coating condition. Little clumping of rice seeds and little production of clumps only made from powders are observed. |
| 15 | Initial stage | Uniform coating condition. Little clumping of rice seeds and little production of clumps only made from powders are observed. |
| 16 | Initial stage | Uniform coating condition. Little clumping of rice seeds and little production of clumps only made from powders are observed. |
| Comparative Example | | |
| 1 | Initial stage | Coated rice seeds and uncoated rice seeds are observed, and therefore, coating is non-uniform. Production of a large amount of clumps only made from powders is observed. |
| | After 60 days at 40° C. | Coated rice seeds and uncoated rice seeds are observed, and therefore, coating is non-uniform. Production of a large amount of clumps only made from powders is observed. |
| 2 | Initial stage | Coated rice seeds and uncoated rice seeds are observed, and therefore, coating is non-uniform. Production of a large amount of clumps only made from powders is observed. |
| | After 60 days at 40° C. | Coated rice seeds and uncoated rice seeds are observed, and therefore, coating is non-uniform. Production of a large amount of clumps only made from powders is observed. |
| 5 | Initial stage | Coated rice seeds and uncoated rice seeds are observed, and therefore, coating is non-uniform. Production of a large amount of clumps only made from powders is observed. |
| | After 60 days at 40° C. | Coated rice seeds and uncoated rice seeds are observed, and therefore, coating is non-uniform. Production of a large amount of clumps only made from powders is observed. |
| 7 | Initial stage | Coated rice seeds and uncoated rice seeds are observed, and therefore, coating is non-uniform. Production of a large amount of clumps only made from powders is observed. |

TABLE 2-continued

| | | Coating condition |
|---|---|---|
| 8 | Initial stage | Coated rice seeds and uncoated rice seeds are observed, and therefore, coating is non-uniform. Production of a large amount of clumps only made from powders is observed. |
| 13 | Initial stage | Coated rice seeds and uncoated rice seeds are observed, and therefore, coating is non-uniform. Production of a large amount of clumps only made from powders is observed. |
| 14 | Initial stage | Coated rice seeds and uncoated rice seeds are observed, and therefore, coating is non-uniform. Production of a large amount of clumps only made from powders is observed. |

Test Example 3

The packaged bags according to Example 6, Example 7, Example 13, Example 14, Comparative Example 3, Comparative Example 4, Comparative Example 5, Comparative Example 9, Comparative Example 10, and Comparative Example 11 were allowed to stand for 60 days at 40° C. The initial number of fungi before packaging and the number of fungi after standing for 60 days at 40° C. were calculated according to the method shown below. In Comparative Example 6 and Comparative Example 12, only the initial number of fungi was calculated.

A composition having pH 6.8, and comprising 0.1% by mass of $KH_2PO_4$, 0.05% by mass of $MgSO_4 \cdot 7H_2O$, 0.5% by mass of peptone, 1% by mass of glucose, 0.003% by mass of rose bengal, and 2% by mass of agarose was employed as a medium, and the number of the living fungi was measured according to a dilution plate technique. In the agar plate media, culture was carried out for 48 hours at 27° C. to form a colony. From the number of formed colonies, the number of the living fungi was estimated. This was employed as a colony forming unit (cfu), that is, the number of the living fungi based on 1 g of the formulation, and was expressed as cfu/g. The results are shown in Table 3.

TABLE 3

| | Number of initial fungi | Number of fungi after storing for 60 days at 40° C. |
|---|---|---|
| Example | | |
| 6 | 4.00 E+08 | 1.30 E+08 |
| 7 | 2.60 E+08 | 8.00 E+07 |
| 13 | 2.60 E+08 | 8.70 E+07 |
| 14 | 2.60 E+08 | 7.50 E+07 |
| Comparative Example | | |
| 3 | 4.00 E+08 | 9.00 E+06 |
| 4 | 4.00 E+08 | 1.00 E+06 |
| 5 | 4.00 E+08 | 8.70 E+06 |
| 6 | 2.30 E+07 | — |
| 9 | 2.60 E+08 | 2.00 E+06 |
| 10 | 2.60 E+08 | 3.30 E+06 |
| 11 | 2.60 E+08 | 1.00 E+07 |
| 12 | 1.20 E+07 | — |

Note)
With respect to the number of fungi in the Table, for example, "4.00 E+08" means "4.00 × $10^8$".

According to the present invention, wettable compositions, for use in agriculture, comprising spores of filamentous fungi as an active ingredient, in which the spores of filamentous fungi described above can be stored over long periods, and which exhibit superior physical properties during applications, can be provided without employing any special preparation methods or treating methods.

What is claimed is:

1. A wettable composition, comprising:

spores of filamentous fungi as an active ingredient supported on an adsorbent having a water absorption ability, wherein the spores of the filamentous fungi are in the form of a dried powder having a volume median diameter ranging from 2 µm to 10 µm, and having a ratio of (volume 90% diameter)/(volume 10% diameter) of not more than 5.62, wherein the adsorbent is present in the composition in an amount of at least 1% by weight based on the total weight of the composition which is useful in agriculture.

2. The wettable composition according to claim 1, wherein the filamentous fungi are selected from the group consisting of filamentous fungi belonging to the genus Trichoderma and the genus Aspergillus.

3. The wettable composition according to claim 1, wherein the adsorbent having a water absorption ability has an ability to absorb moisture in an amount of 10% or more by weight based on the weight of the adsorbent itself.

4. The wettable composition according to claim 1, wherein the adsorbent having a water absorption ability is at least one substance selected from the group consisting of a synthetic zeolite, silica gel, and alumina.

5. The wettable composition according to claim 1, wherein the adsorbent is a synthetic zeolite employed in the range of 1 to 25% by weight based on the total weight of the composition.

6. The wettable composition according to claim 1, wherein the adsorbent is silica gel employed in the range of 50 to 95% by weight based on the total weight of the composition.

7. The wettable composition according to claim 1, wherein the adsorbent is alumina employed in the range of 10 to 95% by weight based on the total weight of the composition.

8. The wettable composition according to claim 1, further comprising a surfactant.

9. The wettable composition according to claim 8, wherein said surfactant is a nonionic surfactant, an anionic surfactant, an alkylsulfuric ester, an alkylphosphoric ester, an alkylaryl sulfuric ester, an alkylarylphosphoric ester, polyoxyethyene ether sulfuric ester, a polyoxyethylene alkylaryl ether sulfuric ester, a polyoxyethylene allyl phenyl ether phosphate, a polycarboxylic acid polymer activator, a silicone-based surfactant, a fluorine-based surfactant, or a soap surfactant.

10. The wettable composition according to claim 8, wherein the content of surfactant in the composition ranges from 0.1–20% by weight of the composition.

11. The wettable composition according to claim 10, wherein the content of surfactant ranges from 0.5–10% by weight, based on the total weight of the composition.

12. The wettable composition according to claim 1, further comprising a carrier.

13. The wettable composition according to claim 12, wherein said carrier is a water-soluble carrier which is a salt of an organic or inorganic acid.

14. The wettable composition according to claim 12, wherein said carrier is a water-insoluble carrier.

15. The wettable composition according to claim 1, which has a moisture content in an amount of less than 2.5% by weight based on the total weight of the composition.

16. The wettable composition according to claim 1, which is in the form of granules and contains a binder component.

17. A method for storing a wettable composition, comprising:
packaging the wettable composition according to claim 1 in a bag formed from a hermetic film, thereby effecting storage of the composition for agricultural use.

18. A method for preparing a wettable composition, comprising:
preparing a mixture of spores of filamentous fungi as a dried powder having a volume median diameter ranging from 2 $\mu$m to 10 $\mu$m and having a ratio of (volume 90% diameter)/(volume 10% diameter) of not more than 5.62, an adsorbent having a water absorption ability, and other additive components, in determined amounts;

pulverizing and mixing the mixture by means of impact pulverization; and adjusting the moisture content of the composition so that the moisture content is less than 2.5% by weight based on the total weight of the composition.

* * * * *